United States Patent [19]
Pellicciari et al.

[11] Patent Number: 5,177,109
[45] Date of Patent: Jan. 5, 1993

[54] 2-AMINO-4,5-METHYLENEADIPIC ACID COMPOUNDS FOR TREATMENT OF CNS DISORDERS

[75] Inventors: Roberto Pellicciari; Benedetto Natalini, both of Perugia; Maura Marinozzi, Fermo, all of Italy; Alexis A. Cordi, St. Louis, Mo.; Joseph B. Monahan, Black Jack, Mo.; Thomas H. Lanthorn, Ballwin, Mo.

[73] Assignee: G. D. Searle & Co., Chicago, Ill.

[21] Appl. No.: 732,881

[22] Filed: Jul. 19, 1991

Related U.S. Application Data

[63] Continuation of Ser. No. 194,361, May 16, 1988, abandoned.

[51] Int. Cl.$^5$ .............................................. A61K 31/19
[52] U.S. Cl. .................... 514/572; 514/484; 514/513; 514/531; 514/562; 514/563; 514/570; 514/616; 558/251; 558/254; 558/255; 560/1; 560/16; 560/38; 560/39; 560/41; 560/105; 560/106; 560/115; 560/118; 560/122; 560/123; 560/124; 560/250; 562/426; 562/443; 562/444; 562/450; 562/500; 562/506; 564/153; 564/154; 564/155; 564/157
[58] Field of Search ............ 560/124, 171, 1, 16, 560/38, 39, 41, 115, 118, 122, 123, 105, 106, 250; 562/506, 571, 426, 443, 444, 450, 500; 514/572, 484, 513, 531, 562, 563, 570, 572, 616; 558/251, 254, 255; 564/153, 154, 155, 157

[56] References Cited

FOREIGN PATENT DOCUMENTS
154499 2/1986 Japan.

OTHER PUBLICATIONS
S. M. Rothman and J. W. Olney, *Annals of Neurology*, 19, 105–111 (1986).
M. N. Perkins et al, *Neuroscience Letters*, 23, 333–336 (1981).
J. Davies et al, *Neuroscience Letters*, 21, 77–81 (1981).
K. Matoba et al, *Chem. Pharm. Bull.*, 32, (10), 3918–3925 (1984).
L. Fowden et al, *Phytochemistry*, 8, 437–443 (1969).
K. Yamanoi et al, Tetrahedron Letters, 29, 1181–1184 (1988).
6th Camerino–Noordwijkerhout Symposium: Recent Advances in Receptor Chemistry Abstracts, Camerino, Italy, 73–74 (1987).

Primary Examiner—Michael L. Shippen
Attorney, Agent, or Firm—J. Timothy Keane; Charles E. Smith; Paul D. Matukaitis

[57] ABSTRACT

Compounds, compositions and methods are described for treating a CNS disorder such as a cognitive disorder, epilepsy, depression, Parkinson's disease, Alzheimer's disease, a neurodegenerative disease or neurotoxic injury. Compound of interest are 2-amino-4,5-methyleneadipic acid compounds and derivatives defined by the formula I:

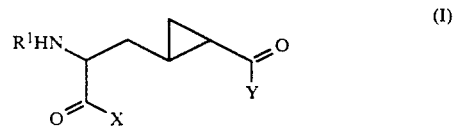

(I)

wherein $R^1$ is selected from hydrido, alkyl, cycloalkyl, aralkyl, aryloxyalkyl, arylthioalkyl,

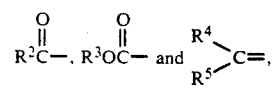

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

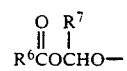

with each of $R^6$ and $R^7$ being independently selected from hydrido, alkyl, cycloalkyl, aryl and aralkyl; wherein any of $R^1$ through $R^7$ groups having a substitutable position may be substituted with one or more substituents selected from hydroxyl, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

20 Claims, No Drawings

2-AMINO-4,5-METHYLENEADIPIC ACID COMPOUNDS FOR TREATMENT OF CNS DISORDERS

This is a continuation of application Ser. No. 07/194,361 filed May 16, 1988, now abandoned.

FIELD OF THE INVENTION

This invention is in the field of clinical neurology and relates specifically to a class of therapeutically useful compounds, compositions and methods for management of neurotoxic damage, epilepsy, memory disorders and neurodegenerative diseases. For example, these compounds are particularly useful for treating neurotoxic injury which follows periods of anoxia or ischemia associated with stroke, cardiac arrest or perinatal asphyxia. The compounds would also be useful as anticonvulsants and for memory enhancement.

BACKGROUND OF THE INVENTION

Unlike other tissues which can survive extended periods of hypoxia, brain tissue is particularly sensitive to deprivation of oxygen or energy. Permanent damage to neurons can occur during brief periods of hypoxia, anoxia or ischemia. Neurotoxic injury is known to be caused or accelerated by certain excitatory amino acids (EAA) found naturally in the central nervous system (CNS). Glutamate (Glu) is an endogenous amino acid which has been characterized as a fast excitatory transmitter in the mammalian brain. Glutamate is also known as a powerful neurotoxin capable of killing CNS neurons under certain pathological conditions which accompany stroke and cardiac arrest. Normal glutamate concentrations are maintained within brain tissue by energy-consuming transport systems. Under low energy conditions which occur during conditions of hypoglycemia, hypoxia or ischemia, cells can release glutamate. Under such low energy conditions the cell is not able to take glutamate back into the cell. Initial glutamate release stimulates further release of glutamate which results in an extracellular glutamate accumulation and a cascade of neurotoxic injury.

It has been shown that the sensitivity of central neurons to hypoxia and ischemia can be reduced by either blockage of synaptic transmission or by the specific antagonism of postsynaptic glutamate receptors [see S. M. Rothman and J. W. Olney, "Glutamate and the Pathophysiology of Hypoxia—Ischemic Brain Damage," *Annals of Neurology,* Vol. 19, No. 2 (1986)]. Glutamate is characterized as a broad spectrum agonist having activity at three neuronal excitatory amino acid receptor sites. These receptor sites are named after the amino acids which selectively excite them, namely: Kainate (KA), N-methyl-D-aspartate (NMDA or NMA) and quisqualate (QUIS).

Neurons which have EAA receptors on their dendritic or somal surfaces undergo acute excitotoxic degeneration when these receptors are excessively activated by glutamate. Thus, agents which selectively block or antagonize the action of glutamate at the EAA synaptic receptors of central neurons can prevent neurotoxic injury associated with anoxia, hypoxia or ischemia caused by stroke, cardiac arrest or perinatal asphyxia.

Aminophosphonic acids have been investigated as neurotransmitter blockers [see M. N. Perkins et al, *Neuroscience Lett.,* 23, 333 (1981); and J. Davies et al, *Neuroscience Lett.,* 21, 77 (1981)]. In particular, compounds such as 2-amino-4-(2-phosphonomethylphenyl)butyric acid and 2-(2-amino-2-carboxy)ethylphenylphosphonic acid have been synthesized for evaluation as antagonists in blocking the action of the neurotransmitter compounds L-glutamic acid and L-aspartic acid [K. Matoba et al, "Structural Modification of Bioactive Compounds II. Syntheses of Aminophosphonic Acids", *Chem. Pharm. Bull.,* 32, (10) 3918–3925 (1984)].

Intact hippocampal structure is necessary for the brain to process information and store it in memory. The phenomenon of "long term potentiation" (LTP) may be the mechanism by which this process occurs. The leading role of NMDA receptors, a sub-type of excitatory amino acid receptor, in LTP has been firmly established by electrophysiological studies. NMDA antagonists such as 2-amino-7-phosphonoheptanoic acid (APH) may inhibit the induction of LTP.

Certain cyclopropyl-substituted amino acids have been isolated from natural plant sources. For example, cis-α-(carboxycyclopropyl)glycine and trans-α-(carboxycyclopropyl)glycine were obtained, respectively, from the seed of Aesculus and Blighia, the cis-isomer having been characterized as a potent inhibitor of mungbean seedling growth [L. Fowden et al, *Phytochemistry,* 8, 437–443 (1969)].

Japanese Patent Application No. 154,499, published on Feb. 17, 1986, describes a series of cyclopropylglycine derivatives for use in foodstuffs, agrochemicals or pharmaceuticals. Certain 3,4-cyclopropylglutamate isomers have been evaluated in an electrophysiology assay involving a periodically oscillating neuron of an African giant snail [K. Yamanoi et al, *Tetrahedron Letters,* 29, 1181–1186 (1988)].

NMDA receptor agonists have been described. For example, trans- and cis-3,4-cyclopropyl glutamates have been evaluated in glutamate subclass receptor binding assays for displacement of radiolabelled L-glutamate, kainate and AMPA, wherein the cis-isomer was found to be an agonist producing changes similar to L-glutamate [*6th Camerino-Noordwijkerhout Symposium: Recent Advances in Receptor Chemistry, Abstracts,* Camerino, Italy, 73–74 (Sept. 1987)].

DESCRIPTION OF THE INVENTION

Treatment of a mammal afflicted by or susceptible to a CNS disorder, such as a cognitive disorder, epilepsy, depression, Parkinson's disease, Alzheimer's disease, a neurodegenerative disease or neurotoxic injury, is provided by administering to the mammal a therapeutically-effective amount of a compound selected from a class of 2-amino-4,5-methyleneadipic acid compounds and derivatives defined by Formula I:

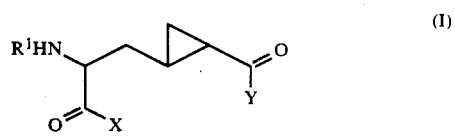

wherein $R^1$ is selected from hydrido, alkyl, cycloalkyl, aralkyl, aryloxyalkyl, arylthioalkyl,

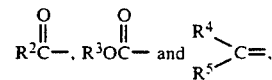

with each of $R^2$, $R^3$, $R^4$ and $R^5$ being independently selected from hydrido, alkyl, cycloalkyl, aryl and aralkyl; wherein each of X and Y is independently selected from hydroxy, alkoxy, alkylthio, amino and

with each of $R^6$ and $R^7$ being independently selected from hydrido, alkyl, cycloalkyl, aryl and aralkyl; wherein any of $R^1$ through $R^7$ groups having a substitutable position may be substituted with one or more substituents selected from hydroxy, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

A preferred class of compounds within Formula I consists of those compounds wherein $R^1$ is selected from hydrido, alkyl, aralkyl,

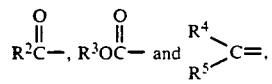

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

with each of $R^6$ and $R^7$ being independently selected from hydrido, alkyl, cycloalkyl, aryl and aralkyl; wherein any of $R^1$ through $R^7$ groups having one or more substitutable positions may be substituted with one or more substituents selected from hydroxy, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

A more preferred class of compounds within Formula I consists of those compounds wherein $R^1$ is selected from hydrido, alkyl, aralkyl,

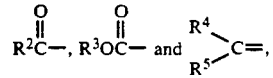

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, amino and

with each of $R^6$ and $R^7$ being independently selected from hydrido, alkyl, cycloalkyl, aryl and aralkyl; wherein any of $R^1$ through $R^7$ groups having one or more substitutable positions on an aryl portion of the group may be substituted with one or more substituents selected from halo, alkyl, hydroxyl, haloalkyl and alkoxy; or a pharmaceutically-acceptable salt thereof.

A further preferred class of compounds within Formula I consists of those compounds wherein $R^1$ is selected from hydrido, linear alkyl, aralkyl,

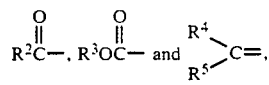

with each of $R^2$, $R^3$, $R^4$ and $R^5$ being independently selected from hydrido, alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

A more highly preferred class of compounds consists of the 2R,4S,5S isomers and the 2R,4R,5R isomers of compounds within Formula I wherein $R^1$ is selected from hydrido, linear alkyl, aralkyl,

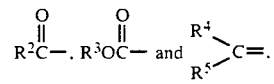

with each of $R^2$, $R^3$, $R^4$ and $R^5$ being independently selected from hydrido, alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

Another more highly preferred class of compounds consists of the 2R,4S,5S isomers and the 2R,4R,5R isomers of compounds within Formula I wherein $R^1$ is selected from hydrido,

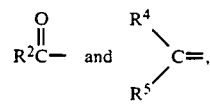

with each of $R^2$, $R^4$ and $R^5$ being independently selected from alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

A most preferred class of compounds within Formula I consists of those compounds wherein $R^1$ is hydrido and each of X and Y is hydroxyl.

Examples of specific most highly preferred compounds within Formula I are 2R,4S,5S-2-amino-4,5-methyleneadipic acid and 2R,4R,5R-2-amino-4,5-methyleneadipic acid.

The term "hydrido" denotes a single hydrogen atom (H) which may be attached, for example, to a carbon atom or to an oxygen atom to form an hydroxyl group. Where the term "alkyl" is used, either alone or within other terms such as "haloalkyl", "aralkyl" and "hydroxyalkyl", the term "alkyl" embraces linear or branched radicals having one to about ten carbon atoms unless otherwise specifically described. Preferred alkyl radicals are "lower alkyl" radicals having one to about five carbon atoms. The term "cycloalkyl" embraces radicals having three to ten carbon atoms, such as cyclopropyl, cyclobutyl, cyclohexyl and cycloheptyl. The term "haloalkyl" embraces radicals wherein any one or more of the carbon atoms is substituted with one or more halo groups, preferably selected from bromo, chloro and fluoro. Specifically embraced by the term "haloalkyl" are monohaloalkyl, dihaloakyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. Examples of a dihaloalkyl group are dibromomethyl, dichloromethyl and bromochloromethyl. Examples of a polyhaloalkyl are trifluoromethyl, 2,2,2-trifluoroethyl, perfluoroethyl and 2,2,3,3-tetrafluoropropyl groups. The term "alkoxy", embraces linear or branched oxy-containing radicals having an alkyl portion of one to about ten carbon atoms, such as methoxy, ethoxy, isopropoxy and butoxy. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals $>SO$ and $>SO_2$. The term "acyl" whether used alone, or within a term such as acyloxy, denotes a radical provided by the residue after removal of hydroxyl from an organic acid, examples of such radical being acetyl and benzoyl.

Within this class of 2-amino-4,5-methyleneadipic acids and derivatives of the invention are the pharmaceutically acceptable salts of the compounds of Formula I, including acid addition salts and base addition salts. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, $\beta$-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I.

Compounds of general Formula 1 can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting compounds of Formula I with an optically pure acid in an activated form or an optically pure isocyanate. The synthesized diastereoisomers can be separated by conventional means such as chromatography, distillation, crystallization or sublimation, and then hydrolyzed to deliver the enantiomericaly pure compound. The optically active compounds of Formula I can likewise be obtained by utilizing optically active starting materials. These isomers may be in the form of a free acid, a free base, an ester or a salt.

The nomenclature used herein for describing isomers of compounds of Formula I is illustrated by reference to the following example:

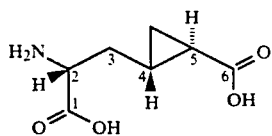

An abbreviated system for referring to mixtures of isomers of compounds of Formula I is illustrated by the following example: trans-D-2-amino-4,5-methyleneadipic acid stands for a mixture of the 4S,5R and 4R,5S isomers and cis-D-2-amino-4,5-methyleneadipic acid stands for a mixture of the 4S,5S and 4R,5R isomers.

Examples of the compounds of Formula I are the following:
- -2R,4S,5R-2-amino-4,5-methylene-adipic acid;
- -2R,4R,5R-2-amino-4,5-methylene-adipic acid;
- -2R,4S,5S-2-amino-4,5-methylene-adipic acid;
- -2R,4R,5S-2-amino-4,5-methylene-adipic acid;
- -2S,4S,5R-2-amino-4,5-methylene-adipic acid;
- -2S,4R,5R-2-amino-4,5-methylene-adipic acid;
- -2S,4S,5S-2-amino-4,5-methylene-adipic acid;
- -2S,4R,5S-2-amino-4,5-methylene-adipic acid;
- -2R,4S,5R-2-amino-4,5-methylene-adipic acid diethyl ester;
- -2R,4R,5R-2-amino-4,5-methylene-adipic acid diethyl ester;
- -2R,4S,5S-2-amino-4,5-methylene-adipic acid diethyl ester;
- -2R,4R,5S-2-amino-4,5-methylene-adipic acid diethyl ester;
- -2S,4S,5R-2-amino-4,5-methylene-adipic acid diethyl ester;
- -2S,4R,5R-2-amino-4,5-methylene-adipic acid diethyl ester;
- -2S,4S,5S-2-amino-4,5-methylene-adipic acid diethyl ester;
- -2S,4R,5S-2-amino-4,5-methylene-adipic acid diethyl ester;
- -2R,4S,5R-2-amino-4,5-methylene-adipic acid-1-methyl-6-ethyl ester;
- -2R,4R,5R-2-amino-4,5-methylene-adipic acid-1-methyl-6-ethyl ester;
- -2R,4S,5S-2-amino-4,5-methylene-adipic acid-1-methyl-6-ethyl ester;
- -2R,4R,5S-2-amino-4,5-methylene-adipic acid-1-methyl-6-ethyl ester;
- -2S,4S,5R-2-amino-4,5-methylene-adipic acid-1-methyl-6-ethyl ester;
- -2S,4R,5R-2-amino-4,5-methylene-adipic acid-1-methyl-6-ethyl ester;
- -2S,4S,5S-2-amino-4,5-methylene-adipic acid-1-methyl-6-ethyl ester;
- -2S,4R,5S-2-amino-4,5-methylene-adipic acid-1-methyl-6-ethyl ester;
- -2R,4S,5R-2-acetylamino-4,5-methylene-adipic acid;
- -2R,4R,5R-2-acetylamino-4,5-methylene-adipic acid;
- -2R,4S,5S-2-acetylamino-4,5-methylene-adipic acid;
- -2R,4R,5S-2-acetylamino-4,5-methylene-adipic acid;
- -2S,4S,5R-2-acetylamino-4,5-methylene-adipic acid;
- -2S,4R,5R-2-acetylamino-4,5-methylene-adipic acid;
- -2S,4S,5S-2-acetylamino-4,5-methylene-adipic acid;
- -2S,4R,5S-2-acetylamino-4,5-methylene-adipic acid;
- -2R,4S,5R-2-acetylamino-4,5-methylene-adipic acid diethyl ester;
- -2R,4R,5R-2-acetylamino-4,5-methylene-adipic acid diethyl ester;
- -2R,4S,5S-2-acetylamino-4,5-methylene-adipic acid diethyl ester;
- -2R,4R,5S-2-acetylamino-4,5-methylene-adipic acid diethyl ester;
- -2S,4S,5R-2-acetylamino-4,5-methylene-adipic acid diethyl ester;
- -2S,4R,5R-2-acetylamino-4,5-methylene-adipic acid diethyl ester;
- -2S,4S,5S-2-acetylamino-4,5-methylene-adipic acid diethyl ester;
- -2S,4R,5S-2-acetylamino-4,5-methylene-adipic acid diethyl ester;
- -2R,4S,5R-2-benzyloxycarbonylamino-4,5-methylene-adipic acid diethyl ester;
- -2R,4R,5R-2-benzyloxycarbonylamino-4,5-methylene-adipic acid diethyl ester;
- -2R,4S,5S-2-benzyloxycarbonylamino-4,5-methylene-adipic acid diethyl ester;
- -2R,4R,5S-2-benzyloxycarbonylamino-4,5-methylene-adipic acid diethyl ester;
- -2S,4S,5R-2-benzyloxycarbonylamino-4,5-methylene-adipic acid diethyl ester;
- -2S,4R,5R-2-benzyloxycarbonylamino-4,5-methylene-adipic acid diethyl ester;
- -2S,4S,5S-2-benzyloxycarbonylamino-4,5-methylene-adipic acid diethyl ester;
- -2S,4R,5S-2-benzyloxycarbonylamino-4,5-methylene-adipic acid diethyl ester;
- -2R,4S,5R-2-benzyloxycarbonylamino-4,5-methylene-adipic acid-1-methyl-6-ethyl ester;
- -2R,4R,5R-2-benzyloxycarbonylamino-4,5-methylene-adipic acid-1-methyl-6-ethyl ester;
- -2R,4S,5S-2-benzyloxycarbonylamino-4,5-methylene-adipic acid-1-methyl-6-ethyl ester;
- -2R,4R,5S-2-benzyloxycarbonylamino-4,5-methylene-adipic acid-1-methyl-6-ethyl ester;
- -2S,4S,5R-2-benzyloxycarbonylamino-4,5-methylene-adipic acid-1-methyl-6-ethyl ester;
- -2S,4R,5R-2-benzyloxycarbonylamino-4,5-methylene-adipic acid-1-methyl-6-ethyl ester;
- -2S,4S,5S-2-benzyloxycarbonylamino-4,5-methylene-adipic acid-1-methyl-6-ethyl ester; and
- -2S,4R,5S-2-benzyloxycarbonylamino-4,5-methylene-adipic acid-1-methyl-6-ethyl ester.

GENERAL SYNTHETIC PROCEDURES

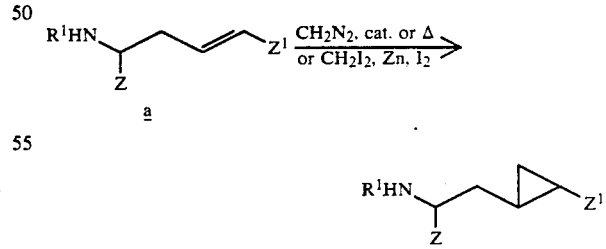

In the synthetic description of compounds of Formula I, Z and $Z^1$ represent independently COX and COY with each of $R^1$, X and Y as defined above for Formula I. Z and $Z^1$ may also represent independently any other group so as to define a precursor which can be transformed easily into a carboxylic acid or one of its derivatives such as cyano, hydroxymethyl, aldehyde, orthoester, amidine, imidate, oxazoline group, or one of their protected forms such as acetal or thioacetal (cyclic or acyclic), tetrahydropyranylether, benzylether, diphenylmethylether or tritylether. Compound I' can thus be a precursor to a compound of Formula I which can be transformed into a carboxylic acid or derivative by hydrolytic or oxidative steps.

In a first method for making of compounds of Formula I, the compounds of general structure I' are obtained by reacting an unsaturated amino adipate derivative with either diazomethane in the presence of a metallic catalyst such as an organic or inorganic salt of copper, palladium, rhodium or diazomethane in the absence of catalyst, leading to the production of a pyrazoline derivative which is optimally transformed into the cyclopropane by heating or by irradiation by UV or visible light, or diiodomethane in the presence of zinc powder and iodine under conditions known as the Simmons-Smith reaction which can be modified by replacement of the zinc-iodine couple by diethylzinc, or trimethylsulfonium iodide known as the Corey reagent. The reaction can be conducted neat or in the presence of a solvent such as an ether (cyclic or acyclic), an alkane, a cycloalkane, an halogenoalkane, an aromatic substituted or unsubstituted, at a temperature between room temperature and the reflux temperature of the solvent used.

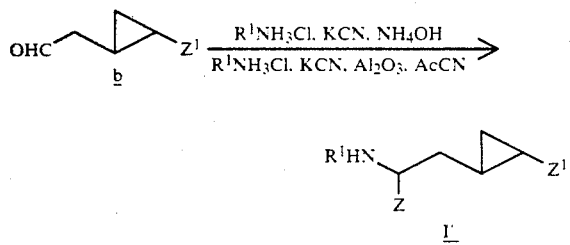

In a second method for making compounds of Formula I, the cyclopropylaldehydes are transformed into the amino nitriles by the Strecker reaction, the reaction is preferably conducted in water or in a protonated solvent, such as a lower alcohol, at room temperature. If solubility problems are encountered, the reaction can be conducted in acetonitrile in the presence of alumina accompanied by irradiation with an ultrasonic source.

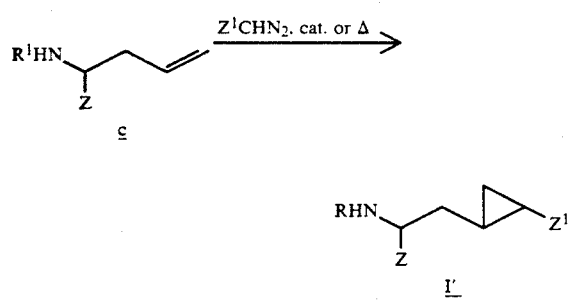

In a third method for making compounds of Formula I, a vinyl or allyl glycine derivative is reacted with a substituted diazoalkane. The reaction is preferably conducted neat or in a non-reacting solvent such as benzene or dichloromethane at the reflux temperature of the solvent or of the reaction mixture, in the presence of a metallic catalyst such as an organic or inorganic salt of copper, palladium, rhodium or ruthenium.

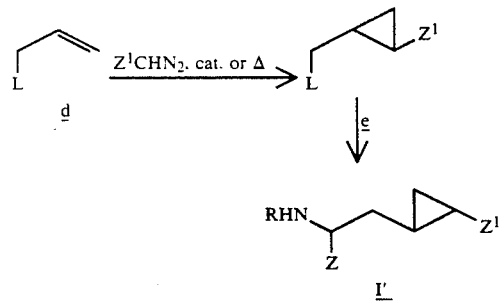

In a fourth method for making compounds of Formula I, an allylic derivative d where L stands for a good leaving group such as chloride, bromide, iodide, tosylate, mesylate or acetate, or a precursor thereof, is reacted with a substituted diazoalkane in conditions described above to yield the cyclopropyl derivative e which can be converted to I' by substitution of the leaving group by a protected glycine anion such as acetamidomalonate anion, ethyl benzilideneaminoacetate anion or ethyl diphenylmethyleneaminoacetate anion. The reaction will be preferably conducted in a protic solvent such as an alcohol in the presence of a base, organic or inorganic, able to generate the anion; alternatively the reaction can also be conducted in an aprotic solvent in the presence of a solid base or an aqueous solution of a strong inorganic base such as NaOH but under the influence of phase transfer catalyst. The reaction temperature is preferably kept low ($-78°$ C.) when the anion is prepared in a separate vessel, but in phase transfer conditions the reaction temperature can be raised to increase the reactivity.

The following Examples I-VI are detailed descriptions of the methods of preparation of compounds of Formula I. These detailed preparations fall within the scope of, and serve to exemplify, the above described General Synthetic Procedures which form part of the invention. These Examples I-VI are presented for illustrative purposes only and are not intended as a restriction on the scope of the invention. All parts are by weight unless otherwise indicated.

EXAMPLE I

N-benzyloxycarbonyl-L-allyglycine (2)

Benzyl chloroformate (1.5 g, 9.0 mmol) was added dropwise in 15 min. to a suspension of L-allylglycine (1.0 g, 8.68 mmol) and sodium hydrogen carbonate (1.8 g) in water (20 ml) kept under vigorous stirring at 0° C. The resulting mixture was stirred at room temperature for 6 hours. The reaction mixture was then washed with ether (2×10 ml), acidified with 6N hydrochloric acid, extracted with ethyl acetate (4×20 ml) and dried over sodium sulfate. Evaporation of the solvent yielded pure 2 $\nu$max (CHCl$_3$) 3440 (OH), 1720 CM$^{-1}$ (CO); $^1$H—NMR (CDCl$_3$) $\delta$ 2.57 (2H, m, 3—CH$_2$); 4.47 (1H, m, 2—CH); 5.12 (4H, m, —CH$_2$Ph and 5—CH$_2$); 5.67 (2H, m, 4—CH and —NH); 7.33 (5H, s, aromatic).

N-benzyloxycarbonyl-L-allylglycine, methyl ester (3)

An ethereal solution of diazomethane (40 ml), prepared from Diazald (4.3 g), was added dropwise in 5 min. to a solution of 2 (1.9 g, 7.9 mmol) in ether (20 ml)

kept under stirring at 0° C. The reaction mixture was stirred at room temperature for 15 min.; a stream of nitrogen was then used to eliminate the excess of diazomethane and the solvent was evaporated in vacuo. Flash chromatography of the residue (1.95 g) and elution with hexane-ethyl acetate 85:15 afforded 3 $\nu$max (CHCl$_3$) 1720 cm$^{-1}$ (CO); $^1$H—NMR (CDCl$_3$) $\delta$ 2.52 (2H, m, 3—CH$_2$); 3.67 (3H, s, —CO$_2$Me); 4.43 (1H, m, 2—CH); 5.10 (4H, m, —CH$_2$Ph and 5—CH$_2$); 5.63 (2H, m, 4—CH and —NH); 7.30 (5H, s, aromatic).

Cis- and trans-L-2-benzyloxycarbonylamino-4,5-methyleneadipic acid, 1-methyl-6-ethyl esters (4 and 5)

A solution of ethyl diazoacetate (2.12 g, 18.6 mmol) in anhydrous dichloromenthane (150 ml) was added dropwise in 12 hours to a solution of 3 (1.6 g, 6.4 mmol) and rhodium (ii) acetate dimer (0.275 g, 0.62 mmol) in anhydrous dichloromethane (50 ml) kept under stirring at room temperature in an argon atmosphere. After evaporation of the solvent, the residue (2.0 g) was submitted to medium pressure chromatography: elution with hexane-ethyl acetate 80:20 afforded the starting material. Following elution with the same solvents afforded a mixture containing the cis esters 4, $\nu$max (CHCl$_3$) 1710 cm$^{-1}$ (CO); mixture of isomers $^1$H—NMR (DCDl$_3$) $\delta$ 0.80-1.95 (4H, br m, cyclopropyl); 1.22 (3H, t, J=7 Hz), —CO$_2$CH$_2$CH$_3$); 2.03 (2H, m, 3—CH$_2$); 3.73 (3H, s, —CO$_2$Me); 4.10 (2H, q, J=7 Hz, —CO$_2$CH$_2$CH$_3$); 4.43 (1H, m, 2-CH); 5.10 (2H, s, —CH$_2$Ph); 5.47 (1H, m, —NH); 7.30 (5H, s, aromatics). Following elution with the same solvents afforded a mixture containing the trans esters 5, $\nu$max (CHCl$_3$) 1710 cm$^{-1}$ (CO); mixture of isomers $^1$H—NMR (CDCl$_3$) $\delta$ 0.48-1.53 (4H, br, m, cyclopropyl); 1.23 (3H, t, J=7 Hz, —CO$_2$CH$_2$CH$_3$); 4.45 (1H, m, 2-CH); 5.10 (2H, s, —CH$_2$Ph); 5.73 (1H, m, —NH); 7.30 (5H, s, aromatic).

EXAMPLE II

Cis-L-2-amino-4,5-methyleneadipic acid (6)

A suspension of 4 (0.600 g, 1.78 mmol) in 6N hydrochloric acid (30 ml) was refluxed for 3 hours. After cooling, the reaction mixture was washed with chloroform (2×10 ml) and evaporated in vacuo. The crude reaction product thus obtained was dissolved in water (10 ml) and neutralized to pH=7 with 10% ammonium hydroxide. The resulting solution was passed through a column of ion exchange resin (1×70 cm, Dowex 100-200mesh, AcO$^-$ form). Elution with water and then with 0.3N acetic acid gave 6 m.p. 289-290° C.; mixture of isomers $^1$H—NMR (D$_2$O) $\delta$ 0.73-2.10 (6H, br, m, 3-CH$_2$ and cyclopropyl); 3.68 (1H, t, J=6 Hz, 2-CH); $^{13}$C-NMR (D$_2$O/DCl) $\delta$ 14.9 and 14.7 (C$_7$); 18.2 and 17.8 (C$_5$); 19.5 and 19.5 (C$_4$); 32.7 and 32.5 (C$_3$); 52.7 and 52.7 (C$_2$); 171.2 and 171.2 (C$_1$); 177.9 and 177.9 (C$_6$); [$\alpha$]$_D$$^{20}$=+16 (C=0.765, H$_2$O). (Found: C, 48.50; H, 6.38; N, 8.05. C$_7$H$_{11}$NO$_4$ requires: C, 48.55; H, 6.40; N, 8.09%).

EXAMPLE III

Trans-L-2-amino-4,5-methyleneadipic acid (7)

A suspension of 5 (1.100 g, 3.27 mmol) in 6N hydrochloric acid (50 ml) was refluxed for 3 hours. After cooling, the reaction mixture was washed with chloroform (2×15 ml) and evaporated in vacuo. The crude reaction product thus obtained was dissolved in water (1×70 cm, Dowex 100-200 mesh, AcO$^-$ form). Elution with water and then with 0.3N acetic acid gave 7 m.p. 222-225° C.; mixture of isomers $^1$N-NMR (D$_2$O) $\delta$ 0.67-2.00 (6H, br, m, 3—CH$_2$ and cyclopropyl); 3.70 (1H, t, J=6 Hz, 2—CH); $^{13}$C-NMR (D$_2$O/DCl) $\delta$ 13.4 and 13.4 (C$_7$); 16.5 and 17.0 (C$_5$); 17.8 and 17.6 (C$_4$); 27.4 and 27.7 (C$_3$); 52.7 and 52.9 (C$_2$); 171.2 and 171.2 (C$_2$); 176.4 and 176.4 and 176.4 (C$_6$); [$\alpha$]$_D$$^{20}$=+20 (C=0.2, H$_2$O). (Found: C, 48.57; H, 6.42; N, 8.11. C$_7$H$_{11}$NO$_4$ requires: C, 48.55; H, 6.40; N, 8.09%).

EXAMPLE IV

N-benzyloxycarbonyl-D-allylglycine (9)

Benzyl chloroformate (1.5 g, 9.0 mmol) was added dropwise in 15 min. to a suspension of D-allylglycine (1.0 g, 8.68 mmol) and sodium hydrogen carbonate (1.8 g) in water (20 m) kept under vigorous stirring at 0° C. The resulting mixture was stirred at room temperature for 7 hours. The reaction mixture was then washed with ether (2×10 ml), acidified with 6N hydrochloric acid, extracted with ethyl acetate (4×20 ml) and dried over sodium sulfate. Evaporation of the solvent yielded pure 9 $\nu$max (CHCl$_3$) 3440 (OH), 1720 cm$^{-1}$ (CO); $^1$H—NMR (CDCl$_3$) $\delta$ 2.57 (2H, m, 3—CH$_2$); 4.47 (1H, m, 2—CH); 5.12 (4H, m, —CH$_2$Ph and 5—CH$_2$); 5.67 (2H, m, 4—CH and —NH); 7.33 (5H, s, aromatics).

N-benzyloxycarbonyl-D-allylglycine, methyl ester (10)

An ethereal solution of diazomethane (45 ml), prepared from Diazald (4.8 g), was added dropwise in 5 min. to a solution of 9 (2.1 g, 8.77 mmol) in ether (20 ml) kept under stirring at 0° C. The reaction mixture was stirred at room temperature for 15 min.; a stream of nitrogen was then used to eliminate the excess of diazomethane and the solvent was evaporated in vacuo. Flash chromatography of the residue and elution with hexane ethyl acetate 85:15 afforded 10 $\nu$max (CHCl$_3$) 1720 cm$^{-1}$ (CO); $^1$H—NMR (CDCl$_3$) $\delta$ 2.52 (2H, m, 3—CH$_2$); 3.67 (3H, s, —CO$_2$Me); 4.43 (1H, m, 2—CH); 5.10 (4H, m, —CH$_2$Ph and 5—CH$_2$); 5.63 (2H, m, 4—CH and —NH); 7.30 (5H, s, aromatic).

Cis- and trans-D-2-benzyloxycarbonylamino-4,5-methyleneadipic acid, 1-methyl-6-ethyl esters (11 and 12)

A solution of ethyl diazoacetate (1.4 g 12.28 mmol) in anhydrous dichloromenthane (100 ml) was added dropwise in 10 hours to a solution of 10 (1.0 g, 3.9 mmol) and rhodium (II) acetate dimer (0.180 g, 0.38 mmol) in anhydrous dichloromethane (30 ml) kept under stirring at room temperature in an argon atmosphere. After evaporation of the solvent, the residue (1.8 g) was submitted to medium pressure chromatography: elution with hexane-ethyl acetate 80:20 afforded the starting material. Following elution with the same solvents afforded of a mixture containing the cis esters 11, $\nu$max (CHCl$_3$) 1720 cm$^{-1}$ (CO); mixture of isomers $^1$H—NMR (DCDl$_3$) $\delta$ 0.75-1.93 (4H, br, m, cyclopropyl); 1.22 (3H, t, J=7, Hz, —CO$_2$CH$_2$CH$_3$); 2.04 (2H, m, 3—CH$_2$); 3.73 (3H, s, —CO$_2$Me); 4.10 (2H, q, J=7, Hz, —CO$_2$CH$_2$CH$_3$); 4.45 (1H, m, 2—CH); 5.11 (2H, s, —CH$_2$Ph); 5.52 (1H, m, —NH); 7.33 (5H, s, aromatic). Following elution with the same solvents afforded of a mixture containing the trans esters 12, $\nu$max (CHCl$_3$) 1720 cm$^{-1}$ (CO); mixture of isomers $^1$H—NMR (CDCl$_3$) $\delta$ 0.60-1.65 (4H, br, m, cyclopropyl); 1.24 (3H, t, J=7, Hz, —CO$_2$CH$_2$CH$_3$) 1.77 (2H, m, 3—CH$_2$); 3.76 (3H, s, —CO$_2$Me); 4.12 (2H, q, J=7, Hz, —CO$_2$CH$_2$CH$_3$); 4.50 (1H, m, 2—CH); 5.12

(2H, s, —CH$_2$Ph); 5.75 (1H, m, —NH); 7.34 (5H, s, aromatic).

EXAMPLE V

Cis-D-2-amino-4,5-methyleneadipic acid (13)

A suspension of 11 (0.270 g, 0.80 mmol) in 6N hydrochloric acid (15 ml) was refluxed for 3 hours. After cooling, the reaction mixture was washed with chloroform (2×5 ml) and evaporated in vacuo. The crude reaction product thus obtained was dissolved in water (10 ml) and neutralized to pH=7 with 10% ammonium hydroxide. The resulting solution was passed through a column of ion exchange resin (1×70 cm, Dowex 100-200 mesh, AcO$^-$ form). Elution with water and then with 0.3N acetic acid gave 13 m.p. 189-190° C.; mixture of isomers $^1$H—NMR (D$_2$O) δ 0.60-2.40 (6H, br, m, 3—CH$_2$ and cyclopropyl); 3.74 (1H, t, J=6, Hz, 2—CH); $^{13}$C—NMR (D$_2$O/DCl) δ 15.0 and 15.0 (C$_7$); 17.8 and 18.2 (C$_5$); 19.5 and 19.5 (C$_4$); 32.4 and 32.6 (C$_3$); 52.6 and 52.6 (C$_2$); 171.3 and 171.3 (C$_1$); 177.9 and 177.9 (C$_6$); [α]$_D$ $^{20}$= −16 (C=0.937, H$_2$O). (Found: C, 48.52; H, 6.45; N, 8.08. C$_7$H$_{22}$NO requires: C, 48.55; H, 6.40; N, 8.09%).

EXAMPLE VI

Trans-D-2-amino-4,5-methyleneadipic acid (14)

A suspension of 12 (0.400 g, 1.19 mmol) in 6N hydrochloric acid (20 ml) was refluxed for 3 hours. After cooling, the reaction mixture was washed with chloroform (2×10 ml) and evaporated in vacuo. The crude reaction product thus obtained was dissolved in water (20 ml) and neutralized to pH=7 with 10% ammonium hydroxide. The resulting solution was passed through a column of ion exchange resin (2×70 cm, Dowex 100-200 mesh, AcO$^-$ form). Elution with water and then with 0.3N acetic acid gave 14 m.p. 225-227° C.; mixture of isomers $^1$H—NMR (D$_2$O) δ 0.60-2.20 (6H, br, m, 3—CH$_2$ and cyclopropyl); 3.80 (1H, t, J=6, Hz, 2—CH); $^{13}$C—NMR (D$_2$O/DCl) δ 13.4 and 13.4 (C$_7$); 16.5 and 17.0 (C$_5$); 17.6 and 17.8 (C$_4$); 27.7 and 27.4 (C$_3$); 52.7 and 52.9 (C$_2$); 171.2 and 171.2 (C$_1$); 176.5 and 176.5 (C$_6$); [α]$_D$ $^{20}$= −22 (C=0.823, H$_2$O). (Found: C, 48.55; H. 6.45; N, 8.12. C$_7$H$_{12}$NO$_4$ requires: C, 48.55 H, 6.40; N, 8.09%).

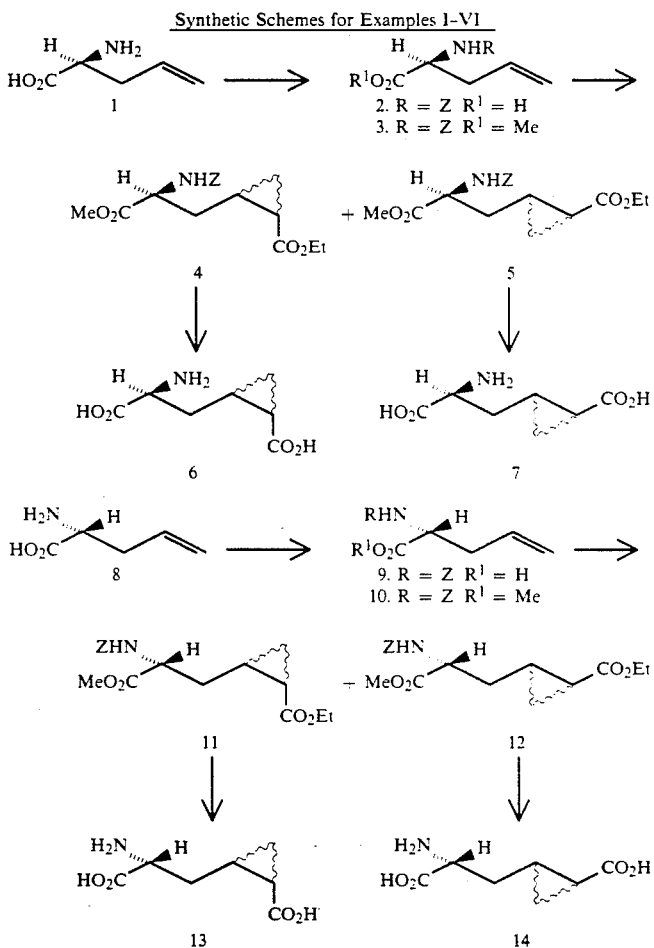

Synthetic Schemes for Examples 1-VI

BIOLOGICAL EVALUATION

Glutamate Binding Assays

The purpose of this assay is to determine the binding affinity of a compound of Formula I for the three glutamic acid receptor sub-types. (NMDA, QUIS, Kainate). It is expected that a compound interacting with one of these sub-type receptors will mimic or antagonize the effect of the endogenous ligand and thereby have a memory enhancing effect or have a neuroprotective and/or anti-epileptic effects. This procedure was carried out as follows:

Synaptic plasma membranes (SPM) were prepared as previously described Montana, J. B. and Michel, J., "Identification and Characterization of an N-methyl-D-aspartate-specific L-[³H]glutamate Recognition Site in Synaptic Plasma Membranes, *J. Neurochem.*, 48, 1699–1708 (1987)]. The SPM were stored at a concentration of 10–15 mg/ml in 0.32M sucrose, 0.5 mM EDTA, 1 mM MgSO₄, 5 mM Tris/SO₄, pH 7.4, under liquid nitrogen. The identity and purity of the subcellular fractions were confirmed by both electron microscopy and marker enzymes. Protein concentrations were determined by using a modification of the method of Lowry [Ohnishi, S. T. and Barr, J. K., "A Simplified Method of Quantitating Proteins Using the Biuret and Phenol Reagents", *Anal. Biochem.*, 86, 193–197 (1978)]. The SPM were treated identically for the [³H]AMPA (QUIS), [³H]kainate and NMDA-specific L-[³H]glutamate binding assays. The SPM were thawed at room temperature, diluted twenty-fold with 50 mM Tris/acetate, pH 7.4, incubated at 37° C. for 30 minutes, and centrifuged at 100,000 g for 15 minutes. The dilution, incubation, and centrifugation was repeated a total of three times. The basic procedure for the receptor subclass binding assays was similar. This general method involved adding the radioligand (12.5 nM L-[³H]glutamate; 0.5 nM [³H]kainate or 10nM [³H]AMPA) to the appropriate concentration of the test compound and initiating the assay by the addition of ice cold SPM (0.2–0.45 mg). The binding assays were performed in 1.5 ml centrifuge tubes with the total volume adjusted to 1.0 ml. Additions of test compounds were made in 50 mM Tris/acetate, pH 7.4 and incubations were carried out at 0–4° C. The incubation time for the NMDA and the AMPA binding assays was 10 minutes and for the kainate binding assay 60 minutes. The AMPA binding assay contained 100 mM KSCN. To terminate the incubation, the samples were centrifuged for 15 minutes at 12,000 g and 4° C. in a Beckman Microfuge 12. The supernatant was aspirated and the pelleted membranes dissolved in Beckman Ready-Protein scintillation cocktail and the samples counted on a Beckman LS 5800 or 3801 liquid scintillation counter with automatic corrections for quenching and counting efficiency. Nonspecific binding was defined as the residual binding in the presence of either excess L-glutamate (0.1 mM), kainate (0.01 mM), or NMDA (0.5 mM), and was typically 15–25% of the total binding in the NMDA binding assay, 19–27% in the AMPA binding assay and 20–30% in the kainate binding assay. Radioligand binding to the SPM was analyzed using Scatchard and Hill transformations and the $K_i$ values of the compounds determined using logit-log transformations. Calculations and regression analysis were performed using templates developed for Lotus 1, 2, 3 as previously described [Pullan, L. M. "Automated Radioligand Receptor Binding Analysis with Templates for Lotus", *Computer Appln. Biosci.*, 3 131 (1987)]. Binding results are reported in Table I for example compounds of the invention.

TABLE 1

| RECEPTOR BINDING DATA | | | |
|---|---|---|---|
| | Binding $K_i$ (μM) | | |
| Compound | NMDA | KA | Quis |
| trans-L-2-amino-4,5-methyleneadipic acid | 2.5 | 37.0 | >300 |
| cis-L-2-amino-4,5-methyleneadipic acid | 14.2 | 23.0 | >300 |
| cis-D-2-amino-4,5-methyleneadipic acid | 1.9 | 13.0 | >300 |
| trans-D-2-amino-4,5-methyleneadipic acid | 2.2 | 25.0 | >300 |

In Vitro Chick Retina Assay

The purpose of this assay is to determine the extent of cell death caused by certain excitotoxins (NMDA, Quis, KA) in the presence and absence of a neuroprotective compound of Formula I. Protection from cell death in this assay by a compound is indicative of the neuroprotective effects which would be exhibited in mammals treated with this compound. This assay is adapted from procedures described in literature sources [Olney, J. W., Price, M. T., Fuller, T. A., Labruyere, J., Samson, L., Carpenter, M., Mahan, K., "The Anti-Excitotoxic Effects of Certain Anesthetics, Analgesics and Sedative-Hypnotics", *Neuroscience Letters*, 68, 29–34, (1986)]. By an approach similar to that earlier described [Reif-Lehrer, L., Bergenthal, J. and Hanninen, L., "Effects of Monosodium Glutamate on Chick Embryo Retina in Culture", *Invest. Ophthalmol.*, 14, 114–124, (1975)], 15-day-old chick embryos were decapitated and their eyes removed and cut into quadrants after excising the cornea and removing the lens, vitreous and iris. The retinal quadrants were then gently separated from the pigment epithelium and incubated for 30 minutes at 37° C. in a standard balanced salt solution (BSS) to which test compounds, either excitatory amino acid agonists or potential antagonists or both, were added in various concentrations. As described elsewhere [Olney, J. W., Price, M. T., Samson, L. and Labruyere, J., "The Role of Specific Ions in Glutamate Neurotoxicity". *Neurosci. Lett.* 65, 65–71, (1986); Price, M. T., Olney, J. W., Samson, L. and Labruyere, J., "Calcium Influx Accompanies But Does Not Cause Excitotoxin-Induced Neuronal Necrosis", *Brain Res. Bull.*, 14, 369–376, (1985)], the BSS contained 140 mM Na⁺, 5.0 mM K⁺, 0.5 mM $Ca^{2+}$, 4.5 mM $Mg^{2+}$, 150 mM Cl⁻ and bicarbonate/phosphate buffer (pH 7.3). After incubation for 30 minutes, the retinal quadrants were fixed by immersion in phosphate-buffered solution containing 1.5glutaraldehyde and 1% paraformaldehyde, then additionally fixed in 1% osmium tetroxide and embedded in araldite, allowing sections to be cut for either light or electron microscopy [Olney, J. W., "Glutamate-Induced Retinal Degeneration in Neonatal Mice. Electron Microscopy of the Acutely Evolving Lesion", *J. Neuropathol. Exp. Neurol.*, 28, 455–474, (1969)]. In pilot studies [Samson, L., Olney, J. W., Price M. T. and Labruyere, J., "Kynurenate Protects Against Excitotoxin-Induced Neuronal Neorosis In Chick Retina", *Soc. Neurosci. Abstr.*, 10, 24, (1984)], it was determined that when the 15-day-old chick embryo retina is incubated for 30 minutes in BSS containing 1 mM Glu, a fully developed lesion occurs resembling that described in the immature mouse retina following s.c. administration of Glu. Other excitotoxin agonists were also found to produce acute lesions within 30 minutes, each agent being effective at a concentration proportional to its known excitatory and toxic potencies (e.g., kainate>quisqualate>N-methyl-D-aspartate>Glu=Asp). The pattern of cellular degeneration was restricted in each case to the ganglion cell, inner plexiform and inner nuclear layers, but within these areas certain agonists induced different patterns of degeneration, the differences being most pronounced between NMDA and KA which we regard as prototypic molecules for inducing distinctive patterns of excitotoxic degeneration. For purposes of the present study, NMDA and KA were the agonists employed and numerous potential antagonists were tested at various concentrations for their ability to prevent NMDA or KA neurotoxicity. The concentrations of NMDA and KA used, 200 and 25 μM, respectively, were those found in pilot experiments to be the lowest concentrations required to consistently obtain fully developed retinal lesions. Although partial blocking was observed for each effective antagonist at concentrations below the threshold for complete protection, the criterion used for comparing agents for antagonist potency is the concentration required to completely prevent NMDA (200 μM) or KA (25 μM) from exerting any toxic activity in any specimen (n>6) studied at that concentration. Internal controls on each experiment consisted of at least 6 specimens being incubated with agonist alone (NMDA 200 μM or KA 25 μM). A typical toxic reaction had to be present in all controls and absent from all experimental specimens in order to qualify as a blocking effect. Results are reported in Table II.

TABLE II

| Compound | Antagonist activity | | |
| --- | --- | --- | --- |
| | vs NMDA μM | vs KA μM | vs QA μM |
| trans-L-2-amino-4,5-methyleneadipic acid | >500 | >500 | >500 |
| cis-L-2-amino-4,5-methyleneadipic acid | >500 | >500 | >500 |
| cis-D-2-amino-4,5-methyleneadipic acid | >75 (100%)* 50 (66%)* 25 (33%)* 10 (0%)* | >500 | >500 |
| trans-D-2-amino-4,5-methyleneadipic acid | >125 (100%)* 75 (66%)* 50 (0%)* | >500 | >500 |

*% protection

[³H]TCP Modulation Assay

The effect on [³H]TCP (1-[1-(2-thienyl)cyclohexyl]-piperidine) binding was measured in rat brain synaptic membranes (SPM) prepared as previously described (J. B. Monahan and J. Michel; J. Neurochem., 48, 1699–1708, (1987)). Prior to their use in the binding assay, frozen SPM were thawed, diluted twenty fold with 50 mM Tris/acetate, pH 7.4 containing 0.04% (v/v) Triton X-100, incubated for 30 min., at 37° C. and centrifuged at 95,000 xspg for 15 min. The Triton X-100 treated SPM were washed with 5 mM Tris/HCl, pH 7.4 and centrifuged a total of six times. The compounds of the invention were incubated with SPM (0.2-0.4 mg protein) and 2 nM [³H]TCP in a total volume of 0.5 ml of 5 mM Tris/HCl buffer pH 7.4 at 25° C. for 60 min. The samples were filtered through glass fiber filters (Schleicher & Schuell #32) which have been pretreated with 0.05% (v/v) polyethylenimine, washed with 2 ml of ice-cold 5 mM Tris/HCl buffer, and then counted on a Beckman LS 5800 liquid scintillation counter with automatic corrections for quenching and counting efficiency. Antagonist character was defined as the ability of the test compound to inhibit [³H]TCP binding in the presence of 1 μM L-glutamate, while agonist character is shown by stimulation of either basal [³H]TCP binding or the binding in the presence of 10 μM D-AP7, a specific competitive NMDA antagonist. Non specific binding was defined as the residual binding in the presence of 60 μM phencyclidine.

Table III shows the result for cis-D-2-amino-4,5-methylene-adipic acid in this assay. In the presence of L-glutamic acid, compound shows an antagonist effect by decreasing the quantity of [³H]TCP specifically bound. In the presence of D-APH, the compound of the invention first shows an agonist effect by increasing quantity of [³H]TCP bound. The maximal stimulation of [³H]TCP binding indued by this compound, however, is substantially less than that shown for the full agonist glutamate. This kind of behavior is characteristic of a partial agonist which can be useful in the treatment of memory disorders without having the potential for neurotoxicity associated with pure agonist molecules.

TABLE III

| cis-D-2-Amino-4,5-methyleneadipic Acid [³H] TCP Bound (DPM) | | |
| --- | --- | --- |
| (μM) | L-Glutamate (1 μM) | D-AP7 (10 μM) |
| 0 | 15466 | 5016 |
| 100 | 12265 | 11453 |
| 200 | 11880 | 11161 |
| 400 | 9622 | 9345 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A compound of the formula

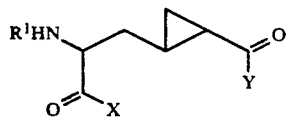

wherein $R^1$ is selected from hydrido, alkyl, cycloalkyl, aralkyl, aryloxyalkyl, arylthioalkyl,

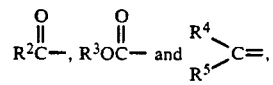

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

with each of $R^6$ and $R^7$ being independently selected from hydrido, alkyl, cycloalkyl, aryl and aralkyl; wherein any of $R^1$ through $R^7$ groups having a substitutable position may be substituted with one or more substituents selected from hydroxyl, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

2. Compound of claim 1 wherein $R^1$ is selected from hydrido, alkyl, aralkyl,

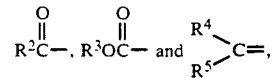

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

with each of $R^6$ and $R^7$ being independently selected from hydrido, alkyl, cycloalkyl, aryl and aralkyl; wherein any of $R^1$ through $R^7$ groups having one or more substitutable positions may be substituted with one or more substituents selected from hydroxyl, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

3. Compound of claim 2 wherein $R^1$ is selected from hydrido, alkyl, aralkyl,

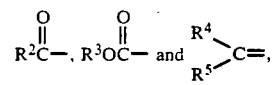

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, amino and

with each of $R^6$ and $R^7$ being independently selected from hydrido, alkyl, cycloalkyl, aryl and aralkyl; wherein any of $R^1$ through $R^7$ groups having one or more substitutable positions on an aryl portion of the group may be substituted with one or more substituents selected from halo, alkyl, haloalkyl, hydroxyl and alkoxy; or a pharmaceutically-acceptable salt thereof.

4. Compound of claim 3 wherein $R^1$ is selected from hydrido, linear alkyl, aralkyl,

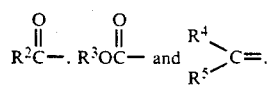

with each of $R^2$, $R^3$, $R^4$ and $R^5$ being independently selected from hydrido, alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

5. Compound of claim 4 selected from the 2R,4S,5S isomers and the 2R,4R,5R isomers wherein $R^1$ is selected from hydrido, linear alkyl, aralkyl,

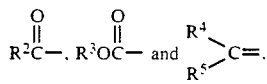

with each of $R^2$, $R^3$, $R^4$ and $R^5$ being independently selected from hydrido, alkyl, aryl and aralkyl; wherein each of X and Y is independently selected from hydroxyl, alkoxy, amino and

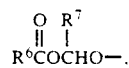

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

6. Compound of claim 5 selected from the 2R,4S,5S isomers and the 2R,4R,5R isomers wherein $R^1$ is selected from hydrido,

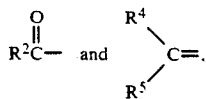

with each of $R^2$, $R^4$ and $R^5$ being independently selected from alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl groups; or a pharmaceutically-acceptable salt thereof.

7. Compound of claim 6 wherein $R^1$ is hydrido and each of X and Y is hydroxyl.

8. Compound of claim 7 selected from the group consisting of
-2R,4S,5R-2-amino-4,5-methylene-adipic acid;
-2R,4R,5R-2-amino-4,5-methylene-adipic acid;
-2R,4S,5S-2-amino-4,5-methylene-adipic acid;
-2R,4R,5S-2-amino-4,5-methylene-adipic acid;
-2S,4S,5R-2-amino-4,5-methylene-adipic acid;
-2S,4R,5R-2-amino-4,5-methylene-adipic acid;
-2S,4S,5S-2-amino-4,5-methylene-adipic acid;
-2S,4R,5S-2-amino-4,5-methylene-adipic acid;
-2R,4S,5R-2-amino-4,5-methylene-adipic acid diethyl ester;
-2R,4R,5R-2-amino-4,5-methylene-adipic acid diethyl ester;
-2R,4S,5S-2-amino-4,5-methylene-adipic acid diethyl ester;
-2R,4R,5S-2-amino-4,5-methylene-adipic acid diethyl ester;
-2S,4S,5R-2-amino-4,5-methylene-adipic acid diethyl ester;
-2S,4R,5R-2-amino-4,5-methylene-adipic acid diethyl ester;
-2S,4S,5S-2-amino-4,5-methylene-adipic acid diethyl ester;
-2S,4R,5S-2-amino-4,5-methylene-adipic acid diethyl ester;
-2R,4S,5R-2-amino-4,5-methylene-adipic acid-1-methyl-6-ethyl ester;
-2R,4R,5R-2-amino-4,5-methylene-adipic acid-1-methyl-6-ethyl ester;
-2R,4S,5S-2-amino-4,5-methylene-adipic acid-1-methyl-6-ethyl ester;
-2R,4R,5S-2-amino-4,5-methylene-adipic acid-1-methyl-6-ethyl ester;
-2S,4S,5R-2-amino-4,5-methylene-adipic acid-1-methyl-6-ethyl ester;
-2S,4R,5R-2-amino-4,5-methylene-adipic acid-1-methyl-6-ethyl ester;
-2S,4S,5S-2-amino-4,5-methylene-adipic acid-1-methyl-6-ethyl ester;
-2S,4R,5S-2-amino-4,5-methylene-adipic acid-1-methyl-6-ethyl ester;
-2R,4S,5R-2-acetylamino-4,5-methylene-adipic acid;
-2R,4R,5R-2-acetylamino-4,5-methylene-adipic acid;
-2R,4S,5S-2-acetylamino-4,5-methylene-adipic acid;
-2R,4R,5S-2-acetylamino-4,5-methylene-adipic acid;
-2S,4S,5R-2-acetylamino-4,5-methylene-adipic acid;
-2S,4R,5R-2-acetylamino-4,5-methylene-adipic acid;
-2S,4S,5S-2-acetylamino-4,5-methylene-adipic acid;
-2S,4R,5S-2-acetylamino-4,5-methylene-adipic acid;
-2R,4S,5R-2-acetylamino-4,5-methylene-adipic acid diethyl ester;
-2R,4R,5R-2-acetylamino-4,5-methylene-adipic acid diethyl ester;
-2R,4S,5S-2-acetylamino-4,5-methylene-adipic acid diethyl ester;
-2R,4R,5S-2-acetylamino-4,5-methylene-adipic acid diethyl ester;
-2S,4S,5R-2-acetylamino-4,5-methylene-adipic acid diethyl ester;
-2S,4R,5R-2-acetylamino-4,5-methylene-adipic acid diethyl ester;
-2S,4S,5S-2-acetylamino-4,5-methylene-adipic acid diethyl ester;

-2S,4R,5S-2-acetylamino-4,5-methylene-adipic acid diethyl ester;
-2R,4S,5R-2-benzyloxycarbonylamino-4,5-methylene-adipic acid diethyl ester;
-2R,4R,5R-2-benzyloxycarbonylamino-4,5-methylene-adipic acid diethyl ester;
-2R,4S,5S-2-benzyloxycarbonylamino-4,5-methylene-adipic acid diethyl ester;
-2R,4R,5S-2-benzyloxycarbonylamino-4,5-methylene-adipic acid diethyl ester;
-2S,4S,5R-2-benzyloxycarbonylamino-4,5-methylene-adipic acid diethyl ester;
-2S,4R,5R-2-benzyloxycarbonylamino-4,5-methylene-adipic acid diethyl ester;
-2S,4S,5S-2-benzyloxycarbonylamino-4,5-methylene-adipic acid diethyl ester;
-2S,4R,5S-2-benzyloxycarbonylamino-4,5-methylene-adipic acid diethyl ester;
-2R,4S,5R-2-benzyloxycarbonylamino-4,5-methylene-adipic acid-1-methyl-6-ethyl ester;
-2R,4R,5R-2-benzyloxycarbonylamino-4,5-methylene-adipic acid-1-methyl-6-ethyl ester;
-2R,4S,5S-2-benzyloxycarbonylamino-4,5-methylene-adipic acid-1-methyl-6-ethyl ester;
-2R,4R,5S-2-benzyloxycarbonylamino-4,5-methylene-adipic acid-1-methyl-6-ethyl ester;
-2S,4S,5R-2-benzyloxycarbonylamino-4,5-methylene-adipic acid-1-methyl-6-ethyl ester;
-2S,4R,5R-2-benzyloxycarbonylamino-4,5-methylene-adipic acid-1-methyl-6-ethyl ester;
-2S,4S,5S-2-benzyloxycarbonylamino-4,5-methylene-adipic acid-1-methyl-6-ethyl ester; and
-2S,4R,5S-2-benzyloxycarbonylamino-4,5-methylene-adipic acid-1-methyl-6-ethyl ester.

9. Compound of claim 8 selected from the group consisting of
2R,4S,5S-2-amino-4,5-methyleneadipic acid and
2R,4R,5R-2-amino-4,5-methyleneadipic acid.

10. Compound of claim 8 selected from the group consisting of
2R,4S,5R-2-amino-4,5-methyleneadipic acid and
2R,4R,5S-2-amino-4,5-methyleneadipic acid.

11. A pharmaceutical composition comprising of an active compound and a pharmaceutically-acceptable carrier or diluent, said active compound selected from a compound of the formula

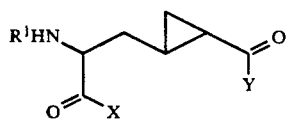

wherein $R^1$ is selected from hydrido, alkyl, cycloalkyl, aralkyl, aryloxyalkyl, arylthioalkyl,

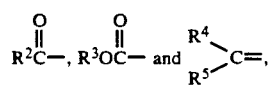

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

with each of $R^6$ and $R^7$ being independently selected from hydrido, alkyl, cycloalkyl, aryl and aralkyl; wherein any of $R^1$ through $R^7$ groups having a substitutable position may be substituted with one or more substituents selected from hydroxyl, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

12. The composition of claim 11 wherein $R^1$ is selected from hydrido, alkyl, aralkyl,

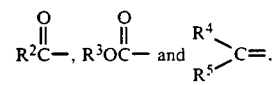

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, alkylthio, amino and

with each of $R^6$ and $R^7$ being independently selected from hydrido, alkyl, cycloalkyl, aryl and aralkyl; wherein any of $R^1$ through $R^7$ groups having one or more substitutable positions may be substituted with one or more substituents selected from hydroxyl, halo, alkyl, haloalkyl, cyano, alkoxy, alkylthio, sulfinyl, sulfonyl, sulfinylalkyl, sulfonylalkyl, amino, acyl, acyloxy, alkoxycarbonyl and aminocarbonyl; or a pharmaceutically-acceptable salt thereof.

13. The composition of claim 12 wherein $R^1$ is selected from hydrido, alkyl, aralkyl,

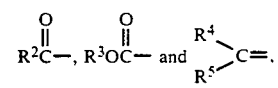

with each of $R^2$, $R^3$, $R^4$ and $R^5$ being independently selected from hydrido, alkyl, cycloalkyl, aryl and aralkyl; wherein each of X and Y is independently selected from hydroxyl, alkoxy, amino and

with each of $R^6$ and $R^7$ being independently selected from hydrido, alkyl, cycloalkyl, aryl and aralkyl; wherein any of $R^1$ through $R^7$ groups having one or more substitutable positions on an aryl portion of the group may be substituted with one or more substituents selected from halo, alkyl, haloalkyl, hydroxyl and alkoxy; or a pharmaceutically-acceptable salt thereof.

14. The composition of claim 13 wherein $R^1$ is selected from hydrido, linear alkyl, aralkyl,

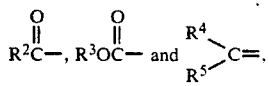

with each of $R^2$, $R^3$, $R^4$ and $R^5$ being independently selected from hydrido, alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo or hydroxyl, groups; or a pharmaceutically-acceptable salt thereof.

15. The composition of claim 14 selected from the 2R,4S,5S isomers and the 2R,4R,5R isomers wherein $R^1$ is selected from hydrido, linear alkyl, aralkyl,

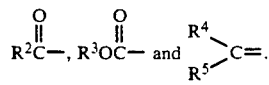

with each of $R^2$, $R^3$, $R^4$ and $R^5$ being independently selected from hydrido, alkyl, aryl and aralkyl; wherein each of X and Y is independently selected from hydroxyl, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo groups; or a pharmaceutically-acceptable salt thereof.

16. The composition of claim 15 selected from the 2R,4S,5S isomers and the 2R,4R,5R isomers wherein $R^1$ is selected from hydrido,

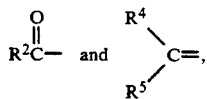

with each of $R^2$, $R^4$ and $R^5$ being independently selected from alkyl, aryl and aralkyl; wherein each of X and Y is independently selected from hydroxy, alkoxy, amino and

with each of $R^6$ and $R^7$ being independently selected from hydrido, alkyl, and aralkyl; wherein any of $R^1$ through $R^7$ groups having one or more substitutable positions on an aryl portion of the group may be substituted with one or more halo groups; or a pharmaceutically-acceptable salt thereof.

17. The composition of claim 16 wherein $R^1$ is hydrido and each of X and Y is hydroxyl.

18. The composition of claim 17 wherein said active compound is selected from the group consisting of
-2R,4S,5R-2-amino-4,5-methylene-adipic acid;
-2R,4R,5R-2-amino-4,5-methylene-adipic acid;
-2R,4S,5S-2-amino-4,5-methylene-adipic acid;
-2R,4R,5S-2-amino-4,5-methylene-adipic acid;
-2S,4S,5R-2-amino-4,5-methylene-adipic acid;
-2S,4R,5R-2-amino-4,5-methylene-adipic acid;
-2S,4S,5S-2-amino-4,5-methylene-adipic acid;
-2S,4R,5S-2-amino-4,5-methylene-adipic acid;
-2R,4S,5R-2-amino-4,5-methylene-adipic acid diethyl ester;
-2R,4R,5R-2-amino-4,5-methylene-adipic acid diethyl ester;
-2R,4S,5S-2-amino-4,5-methylene-adipic acid diethyl ester;
-2R,4R,5S-2-amino-4,5-methylene-adipic acid diethyl ester;
-2S,4S,5R-2-amino-4,5-methylene-adipic acid diethyl ester;
-2S,4R,5R-2-amino-4,5-methylene-adipic acid diethyl ester;
-2S,4S,5S-2-amino-4,5-methylene-adipic acid diethyl ester;
-2S,4R,5S-2-amino-4,5-methylene-adipic acid diethyl ester;
-2R,4S,5R-2-amino-4,5-methylene-adipic acid-1-methyl-6-ethyl ester;
-2R,4R,5R-2-amino-4,5-methylene-adipic acid-1-methyl-6-ethyl ester;
-2R,4S,5S-2-amino-4,5-methylene-adipic acid-1-methyl-6-ethyl ester;
-2R,4R,5S-2-amino-4,5-methylene-adipic acid-1-methyl-6-ethyl ester;
-2S,4S,5R-2-amino-4,5-methylene-adipic acid-1-methyl-6-ethyl ester;
-2S,4R,5R-2-amino-4,5-methylene-adipic acid-1-methyl-6-ethyl ester;
-2S,4S,5S-2-amino-4,5-methylene-adipic acid-1-methyl-6-ethyl ester;
-2S,4R,5S-2-amino-4,5-methylene-adipic acid-1-methyl-6-ethyl ester;
-2R,4S,5R-2-acetylamino-4,5-methylene-adipic acid;
-2R,4R,5R-2-acetylamino-4,5-methylene-adipic acid;
-2R,4S,5S-2-acetylamino-4,5-methylene-adipic acid;
-2R,4R,5S-2-acetylamino-4,5-methylene-adipic acid;
-2S,4S,5R-2-acetylamino-4,5-methylene-adipic acid;
-2S,4R,5R-2-acetylamino-4,5-methylene-adipic acid;
-2S,4S,5S-2-acetylamino-4,5-methylene-adipic acid;
-2S,4R,5S-2-acetylamino-4,5-methylene-adipic acid;
-2R,4S,5R-2-acetylamino-4,5-methylene-adipic acid diethyl ester;
-2R,4R,5R-2-acetylamino-4,5-methylene-adipic acid diethyl ester;
-2R,4S,5S-2-acetylamino-4,5-methylene-adipic acid diethyl ester;
-2R,4R,5S-2-acetylamino-4,5-methylene-adipic acid diethyl ester;
-2S,4S,5R-2-acetylamino-4,5-methylene-adipic acid diethyl ester;
-2S,4R,5R-2-acetylamino-4,5-methylene-adipic acid diethyl ester;
-2S,4S,5S-2-acetylamino-4,5-methylene-adipic acid diethyl ester;
-2S,4R,5S-2-acetylamino-4,5-methylene-adipic acid diethyl ester;

-2R,4S,5R-2-benzyloxycarbonylamino-4,5-methylene-adipic acid diethyl ester;
-2R,4R,5R-2-benzyloxycarbonylamino-4,5-methylene-adipic acid diethyl ester;
-2R,4S,5S-2-benzyloxycarbonylamino-4,5-methylene-adipic acid diethyl ester;
-2R,4R,5S-2-benzyloxycarbonylamino-4,5-methylene-adipic acid diethyl ester;
-2S,4S,5R-2-benzyloxycarbonylamino-4,5-methylene-adipic acid diethyl ester;
-2S,4R,5R-2-benzyloxycarbonylamino-4,5-methylene-adipic acid diethyl ester;
-2S,4S,5S-2-benzyloxycarbonylamino-4,5-methylene-adipic acid diethyl ester;
-2S,4R,5S-2-benzyloxycarbonylamino-4,5-methylene-adipic acid diethyl ester;
-2R,4S,5R-2-benzyloxycarbonylamino-4,5-methylene-adipic acid-1-methyl-6-ethyl ester;
-2R,4R,5R-2-benzyloxycarbonylamino-4,5-methylene-adipic acid-1-methyl-6-ethyl ester;
-2R,4S,5S-2-benzyloxycarbonylamino-4,5-methylene-adipic acid-1-methyl-6-ethyl ester;
-2R,4R,5S-2-benzyloxycarbonylamino-4,5-methylene-adipic acid-1-methyl-6-ethyl ester;
-2S,4S,5R-2-benzyloxycarbonylamino-4,5-methylene-adipic acid-1-methyl-6-ethyl ester;
-2S,4R,5R-2-benzyloxycarbonylamino-4,5-methylene-adipic acid-1-methyl-6-ethyl ester;
-2S,4S,5S-2-benzyloxycarbonylamino-4,5-methylene-adipic acid-1-methyl-6-ethyl ester; and
-2S,4R,5S-2-benzyloxycarbonylamino-4,5-methylene-adipic acid-1-methyl-6-ethyl ester.

19. The composition of claim 18 wherein said active compound is selected from the group consisting of 2R,4S,5S-2-amino-4,5-methyleneadipic acid and 2R,4R,5R-2-amino-4,5-methyleneadipic acid.

20. The composition of claim 18 wherein said active compound is selected from the group consisting of 2R,4S,5R-2-amino-4,5-methyleneadipic acid and 2R,4R,5S-2-amino-4,5-methyleneadipic acid.

* * * * *